United States Patent [19]

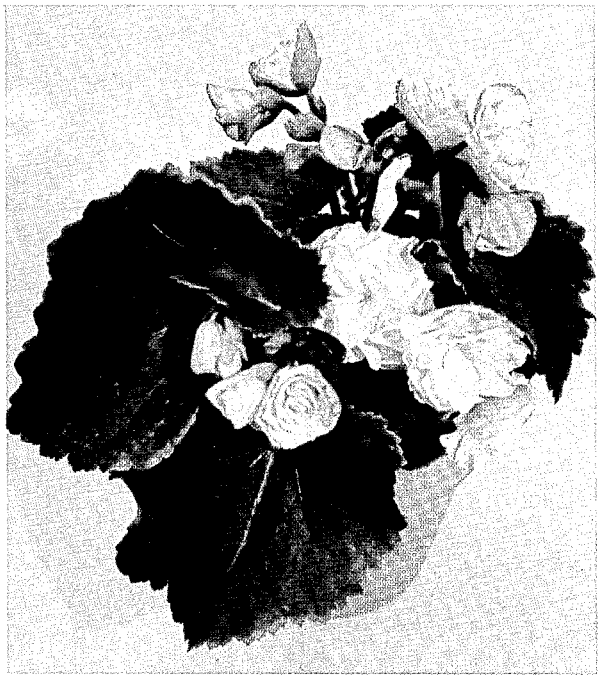

Joachim-Rohde

[11] Plant 4,127

[45] Oct. 18, 1977

[54] BEGONIA PLANT

[75] Inventor: Hans Joachim-Rohde, Nurtingen, Germany

[73] Assignee: Mikkelsens, Inc., Ashtabula, Ohio

[21] Appl. No.: 715,142

[22] Filed: Aug. 17, 1976

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

This mutation of Ballerina principally differs therefrom by its smaller flowers which are more orange.

1 Drawing Figure

1

The present invention relates to a new and distinctive cultivar of begonia plant, botanically known as *begonia elatior* (hiemalis-Fotsch) and known by the cultivar name BALUGA.

The new cultivar was discovered by me as a mutation of the cultivar Ballerina, disclosed in U.S. Plant Pat. No. 3,868, issued Apr. 20, 1976 to Margarete Rohde-Rieger. The new cultivar was observed in a group of flowering plants of the parent cultivar.

Asexual reproduction by stem and/or leaf cuttings has reproduced the unique features of the new cultivar through successive propagations.

The following characteristics in combination distinguish the new begonia from both its parent and other begonias commercially known and used in the floriculture industry:

1. In comparison to Ballerina, the new cultivar has smaller flowers by 10 to 15 mm. and is more orange than apricot in color.
2. Flowers are double with odd numbers of tepals, varying in number more or less from 21 to 31.
3. The growth of the new cultivar is somewhat slower than the parent cultivar Ballerina.
4. General plant characteristics somewhat resembles the Rieger Aphrodite types, but better stem vigor allows this new cultivar to be better adapted to upright growth. Reference is made to U.S. Plant Pat. No. 3,318 (Aphrodite Pink) and U.S. Plant Pat. No. 3,319 (Aphrodite Cherry Red).
5. The new cultivar is highly resistant to common, powdery mildew.
6. Individual flowers are extremely long lasting (up to two months) which is of great value to the producer by allowing a wide spread selling period.
7. Applications of cycocel intensifies the flower color toward orange.
8. BALUGA is more compact and shorter than the parent cultivar Ballerina. Because of this characteristic, BALUGA is better adapted to production in four to five inch pots than Ballerina.

The accompanying colored photograph illustrates the overall appearance of the new cultivar taken as a face view of the plant. The photograph shows the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

2

Parentage: The new cultivar is a mutation of the cultivar Ballerina.

Propagation: Propagation is very rapid by leaf cuttings, being essentially the same as Ballerina and two weeks faster than Schwabenland, disclosed in U.S. Plant Pat. No. 3,320, granted Mar. 13, 1973 to Otto Rieger, deceased. Initiation and development of 3-6 adventitious buds is very consistant at all times of the year and especially good in summer months when the Schwabenland types are inconsistent. Stem cuttings may also be used for propagation as there is considerable self-branching.

Rooting habits: Very easy to root at 20°-22° C. Roots are abundant, fibrous, and have a dendritic pattern.

Plant form: Basically upright, tending to be vining under high light environments.

Habit of growth: Very free growing, but relatively short and compact.

Blooming habits: After flower initiation, there is profuse blooming over a long period of time.

Blooming season: Natural flowering season is in Nov. in Germany. By use of controlled environments of temperature and daylight Ballerina can be commercially produced anytime.

Foliage: Near average for this type of begonia.

Size: 12 to 14 cm. across by up to 10 cm. long. Leaf size will vary with growing conditions.

Shape: Nearly round.

Texture: Leathery.

Margin: Slightly crenate, serrated.

Color:

*Young leaves.*—Upper side, darker than 147A green. Lower side, green mixed with red.

*Mature leaves.*—Upper side, darker than 139A green. Lower side, 147C yellow green.

Disease resistance: More resistant to powdery mildew than the Schwabenland types but somewhat less resistant than the Aphrodite types when all are tested under conditions for optimum mildew growth.

FLOWERS

Borne: On strong upright peduncles. Flowers are double with average of 25 tepals. Odd numbers of tepals usually occur. Edges of flowers are sometimes very wavy.

Quantity: Average for elatior type begonias. Long lasting double flowers and variable color tones give an appearance of greater flowering.

Buds: Flat, measuring 25 mm. in diameter before flowering.

Tepals: Total flower size 35 mm. to 50 mm. in diameter.

Color: The outer two tepals are near orange-red 33A on top and red 43 B-C underside. The secondary tepals range between orange-red 28-C to 29-A top and 38 A-B underside. There is general fading to 21D to 22C.

I claim:

1. A new and distinct cultivar of begonia plant characterized particularly as to uniqueness by the combined characteristics of orange flower; double flowers with odd number of tepals; compact and relatively short growing habit, and long lasting individual flowers which last up to 2 months.

* * * * *

UNITED STATES PATENT AND TRADEMARK OFFICE

CERTIFICATE OF CORRECTION

PATENT NO. : PP-4127

DATED : October 18, 1977

INVENTOR(S) : HANS-JOACHIM ROHDE

It is certified that error appears in the above-identified patent and that said Letters Patent are hereby corrected as shown below:

In Column 2, line 24, "Ballerina" should be "Baluga".

Signed and Sealed this

*Twenty-first* Day of *March 1978*

[SEAL]

*Attest:*

RUTH C. MASON
*Attesting Officer*

LUTRELLE F. PARKER
*Acting Commissioner of Patents and Trademarks*